United States Patent [19]

Zook

[11] Patent Number: 4,775,470
[45] Date of Patent: Oct. 4, 1988

[54] DIAPHRAGM WITH MAGNET

[75] Inventor: James L. Zook, Denver, Colo.

[73] Assignee: Cobe Laboratories, Inc., Lakewood, Colo.

[21] Appl. No.: 865,526

[22] Filed: May 20, 1986

[51] Int. Cl.$^4$ ............................................. B01D 13/00
[52] U.S. Cl. ........................... 210/321.71; 210/321.72
[58] Field of Search ............... 417/393; 222/249, 250; 210/321.3, 321.71, 321.72

[56] References Cited

U.S. PATENT DOCUMENTS

| | | | |
|---|---|---|---|
| 4,077,882 | 3/1978 | Gangemi | 210/94 X |
| 4,204,538 | 5/1980 | Cannon | 222/386.5 X |
| 4,530,759 | 7/1985 | Schal | 210/104 |

FOREIGN PATENT DOCUMENTS

| | | | |
|---|---|---|---|
| 1077943 | 11/1954 | France | 222/249 |
| 164137 | 8/1964 | U.S.S.R. | 222/249 |

Primary Examiner—Frank Spear

[57] ABSTRACT

A diaphragm for use in a fluid flow chamber comprising a generally flat flexible sheet that is engageable at its periphery and has a central portion that is reciprocally movable along an axis perpendicular to a plane through the periphery, the flexible sheet having annular corrugations around the center portion, and a magnet secured to the center of the sheet, the magnet having a front and a rear, the corrugations causing the front and rear to maintain their orientation with respect to the axis as the central portion travels along the axis.

19 Claims, 1 Drawing Sheet

U.S. Patent  Oct. 4, 1988  4,775,470

DIAPHRAGM WITH MAGNET

FIELD OF THE INVENTION

The invention relates to diaphragms useful in fluid flow chambers, in particular to diaphragms used in balance chambers of a dialysate supply machine.

BACKGROUND OF THE INVENTION

Diaphragms can be used in fluid flow chambers to divide the chambers into regions of varying volume. For example, Schal U.S. Pat. No. 4,530,759, which is hereby incorporated by reference, discloses a dialysate supply machine that employs a balance chamber having rigid outer walls and a diaphragm that divides the chamber into two regions so that as one region is being filled with fresh dialysate the other is discharged of an equal amount of spent dialysate as the diaphragm moves toward one of the rigid walls. When all of the spent dialysate has been discharged from the region, the valves at inlets and outlets to the regions are switched, and the spent dialysate side is filled, as the fresh dialysate side discharges, and the diaphragm moves toward the other wall, until all fresh dialysate has been discharged, and so on.

SUMMARY OF THE INVENTION

I have discovered that a diaphragm for use in a fluid flow chamber can be very desirably provided by a flexible sheet carrying a magnet at its center, to permit remote sensing of its position in the chamber, and annular corrugations in the sheet, to cause the front and rear of the magnet to maintain their orientation with respect to an axis of travel for the center of the sheet. When used in a balance chamber provided with hall effect sensors, the maintenance of the orientation of the magnets avoids distortion to signals that could result, e.g., if the faces of the magnet tilted while passing through the center.

In preferred embodiments the magnet is between surface layers of the flexible sheet; the flexible sheet is made of rubber; the corrugations are semicircular in cross-section and contiguous with adjacent corrugations; and the diaphragm is used in a balance chamber of a dialysate supply machine.

Other advantages and features of the invention will be apparent from the claims and from the following description of a preferred embodiment thereof.

DESCRIPTION OF THE PREFERRED EMBODIMENT

The drawings will be briefly described first.

Drawings

STRUCTURE

Figure 1:
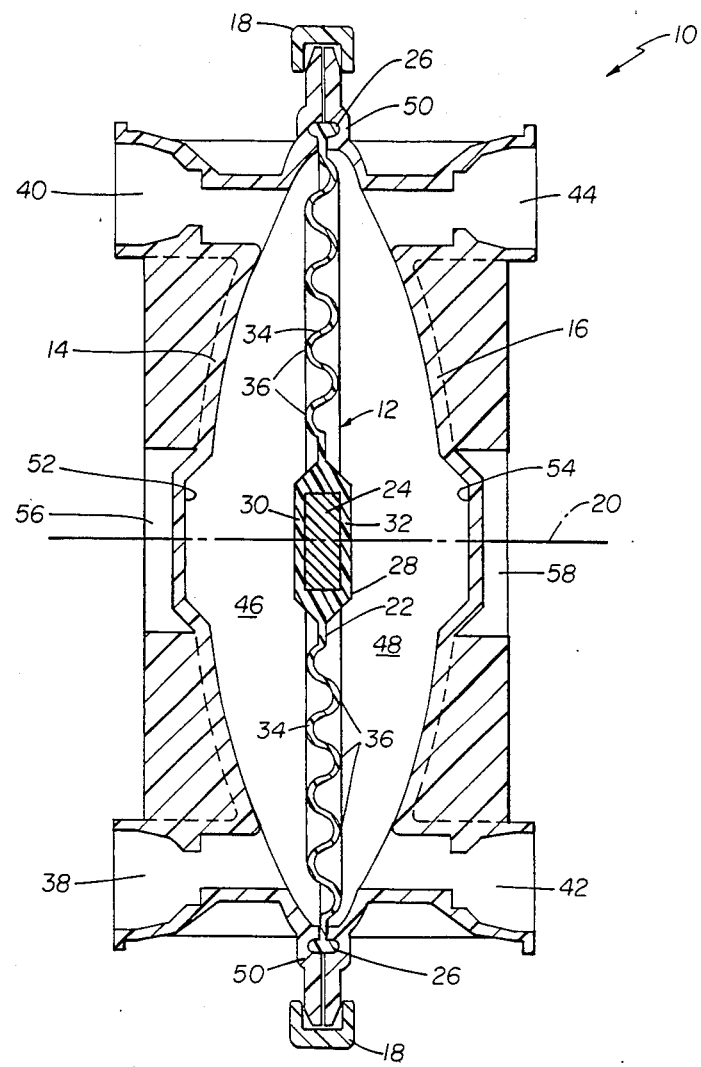
FIG. 1 is a vertical sectional view showing a diaphragm mounted between rigid walls of a balance chamber according to the invention.

Referring to FIG. 1, there is shown balance chamber 10 including diaphragm 12, rigid walls 14, 16 and peripheral clamp 18.

Diaphragm 12 is symmetrical about horizontal axis 20 and includes generally flat flexible rubber sheet 22 and magnet 24. Sheet 22 is made of ethylene propylene elastomer (available from Bellofram Corp. under the trade designation 270–968) and includes peripheral sealing bead 26 (0.150" in axial direction and 0.060" thick in radial direction), center portion 28, including 0.06±0.02" thick layers 30, 32 on the front and back of magnet 24, and 0.030" thick intermediate corrugated portion 34, including eight annular corrugations 36. The overall thickness of corrugated portion 36 (i.e., the distance along an axis parallel to axis 20) is 0.180"; the dimension of each corrugation along an axis perpendicular to axis 20 is 0.186", and the radius of curvature of each corrugated portion 36 is about 0.105", making the shape of each corrugation 36 in cross-section slightly less than a half circle.

Magnet 24 is 0.49±0.01" in diameter, is 0.19±0.01" thick, and is made of ceramic material (barrium or strontium ferrite, Grade 5, oriented and sintered, available from Magnetic Sales and Manufacturing Co., Culver City, Calif.), and molded within flexible sheet 22 in a demagnetized condition (to avoid attracting dirt during manufacture), and magnetized thereafter, having a north pole at one face and a south pole at the other.

Rigid wall 14 has inlet 38 and outlet 40 for fresh dialysate, and rigid wall 16 similarly has inlet 42 and outlet 44 for spent dialysate. Variable volume region 46 between wall 14 and diaphragm 12 is a fresh dialysate region, and variable volume region 48 between diaphragm 12 and wall 16 is a spent dialysate region. Near the peripheries of walls 14, 16 are annular recesses 50 for receiving peripheral sealing bead 26.

Figure 2:
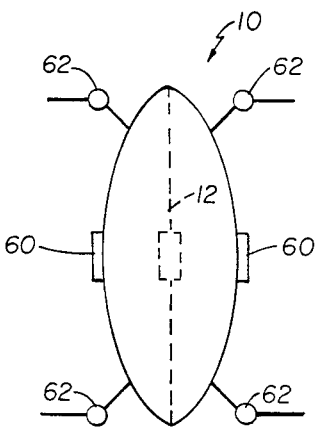
FIG. 2 is a schematic showing use of the FIG. 1 chamber with magnetic position sensors and valves in a dialysate supply machine.

Rigid walls 14, 16 define recessed regions 52, 54 for receiving center portion 28 of diaphragm 12. Cavities 56, 58, outside and adjacent to recessed regions 52, 54, are for receiving hall effect sensors 60 (FIG. 2) used to sense the position along travel axis 20 of magnet 24 and to switch valves 62 operating and closing inlets 38, 42 and outlets 40, 44.

Operation

Balance chamber 10 is used connected in parallel with an identical balance chamber in a dialysate supply machine. Inlet 38 is connected to a source of fresh dialysate; outlet 40 is connected to a dialyzer; inlet 42 is connected to receive spent dialysate from a dialyzer, and outlet 44 is connected to a drain. Valves to inlets 38, 42 and outlets 40, 44 are controlled so that one balance chamber is receiving, in its region 46, fresh dialysate from a source and discharging spent dialysate from its region 48 to a drain (valves to inlet 38 and outlet 44 being open, valves to outlet 40 and inlet 42 being closed, diaphragm 12 moving to the right) while the other is providing fresh dialysate from its region 46 to the dialyzer and receiving spent dialysate in its region 48 from the dialyzer (valves to outlet 40 and inlet 42 being open, valves to inlet 38 and outlet 44 being closed, diaphragm 12 moving to the left).

Travel of diaphragm 12 from one rigid wall to the other is sensed by hall effect sensors 60 in cavities 56, 58. When it is sensed that a diaphragm is just about to bottom out against a wall, the valves to the inlets and outlets are switched, to cause the diaphragms to travel in the other direction. Because of corrugations 36, diaphragm 12 remains symmetrical about axis 20 as it travels along axis 20 in a rolling fashion so that the front and back (north and south) faces of magnet 24 maintain their perpendicular orientation to axis 20, avoiding distortions in the signals of the hall effect sensors sensing magnet position. Between corrugations, there are no flat portions, which might cause stress and inhibit rolling. The equal number of corrugations on each side of the diaphragm are used to equalize forces in travel in both directions. Preferably the corrugations have a uniform radius of curvature and are 180° or less.

Other Embodiments

Other embodiments of the invention are within the scope of the following claims.

What is claimed is:

1. A diaphragm for use in a fluid flow chamber comprising
a generally flat flexible sheet that is engageable at its periphery and has a central portion that is reciprocally movable a first distance between forward and backward positions along an axis perpendicular to a plane through said periphery,
said flexible sheet having annular corrugations around said central portion, and
a magnet secured to said central portion of said sheet, said magnet having a front and a rear spaced from each other along said axis by a distance less than said first distance and adapted to be supported solely by said flexible sheet,
said corrugations causing said front and rear to maintain their orientation with respect to said axis as said central portion travels along said axis.

2. The diaphragm of claim 1 wherein said central portion comprises layers on each side of said magnet.

3. The diaphragm of claim 1 wherein said flexible sheet is made of rubber.

4. The diaphragm of claim 1 wherein said corrugations are arcuate in cross-section.

5. The diaphragm of claim 4 wherein there are an equal number of corrugations on each side of said sheet.

6. The diaphragm of claim 5 wherein said corrugations have a generally uniform radius of curvature.

7. The diaphragm of claim 6 wherein each said corrugation is less than or equal to 180°.

8. The diaphragm of claim 4 wherein said corrugations are contiguous.

9. The diaphragm of claim 2 wherein there are an equal number of corrugations on each side of said sheet, the corrugations have a generally uniform radius of curvature, each corrugation is less than or equal to 180°, and said corrugations are contiguous.

10. A fluid flow chamber comprising
rigid walls having center portions that are spaced further from each other than peripheral portions, said walls defining a chamber therebetween,
a generally flat flexible sheet that is sealably engaged between said perpheral portions and has a central portion that is reciprocally movable a first distance between forward and backward positions along an axis perpendicular to a plane through said periphery,
said flexible sheet having annular corrugations around said central portions, and
a magnet carried solely by said central portion of said sheet and movable therewith back and forth between said walls completely within said chamber,
said magnetic having a front and a rear spaced from each other along said axis by a distance less than said first distance,
said corrugations causing said front and rear to maintain their orientation with respect to said axis as said central portion travels along said axis.

11. The chamber of claim 10 wherein said central portion comprises layers on each side of said magnet.

12. The chamber of claim 10 wherein said corrugations are arcuate in cross-section.

13. The chamber of claim 10 wherein said corrugations are contiguous.

14. The chamber of claim 11 wherein there are an equal number of corrugations on each side of said sheet, the corrugations have a generally uniform radius of curvature, each corrugation is less than or equal to 180°, and said corrugations are contiguous.

15. A dialysate supply machine comprising
a fluid flow chamber with a first inlet for connection to a source of fresh dialysate, a first outlet for connection to a dialyzer, a second inlet for connection to said dialyzer, a second outlet for connection to a drain,
valves controlling flow into and out of said inlets and outlets,
a generally flat flexible sheet within said chamber and dividing said chamber into a fresh dialysate region communicating with said first inlet and outlet and a spent dialysate region communicating with said second inlet and outlet, said generally flat flexible sheet having a periphery sealed to said chamber and a central portion that is reciprocally movable along an axis perpendicular to a plane through said periphery,
said flexible sheet having annular corrugations around said central portion,
a magnet carried solely by said central portion of said sheet and movable therewith back and forth between said walls completely within said chamber,
said magnet having a front and a rear spaced from each other along said axis by a distance less than said first distance,
said corrugations causing said front and rear to maintain their orientation with respect to said axis as said central portion travels along said axis, and
a magnet position sensor outside of said chamber controlling said valves in response to the position of said magnet.

16. The machine of claim 15 wherein said central portion comprises layers on each side of said magnet.

17. The diaphragm of claim 15 wherein said corrugations are arcuate in cross-section.

18. The diaphragm of claim 15 wherein said corrugations are contiguous.

19. The diaphragm of claim 16 wherein there are an equal number of corrugations on each side of said sheet, the corrugations have a generally uniform radius of curvature, each corrugation is less than or equal to 180°, and said corrugations are contiguous.

* * * * *